(12) United States Patent
Marini et al.

(10) Patent No.: US 9,572,767 B2
(45) Date of Patent: Feb. 21, 2017

(54) LUMINATE HAND CREAM

(71) Applicant: Jan Marini Skin Research, San Jose, CA (US)

(72) Inventors: Jan L. Marini, San Jose, CA (US); Subhash J. Saxena, Ringoes, NJ (US)

(73) Assignee: Jan Marini Skin Research, San Jose, CA (US)

( * ) Notice: Subject to any disclaimer, the term of this patent is extended or adjusted under 35 U.S.C. 154(b) by 0 days.

(21) Appl. No.: 14/717,818

(22) Filed: May 20, 2015

(65) Prior Publication Data

US 2016/0338943 A1    Nov. 24, 2016

(51) Int. Cl.

| | | |
|---|---|---|
| *A61K 36/00* | (2006.01) |
| *A61K 8/97* | (2006.01) |
| *A61K 8/92* | (2006.01) |
| *A61K 8/34* | (2006.01) |
| *A61K 8/362* | (2006.01) |
| *A61K 8/49* | (2006.01) |
| *A61K 8/60* | (2006.01) |
| *A61K 8/37* | (2006.01) |
| *A61K 8/891* | (2006.01) |
| *A61Q 19/08* | (2006.01) |
| *A61Q 19/02* | (2006.01) |
| *A61Q 19/00* | (2006.01) |

(52) U.S. Cl.
CPC ................ *A61K 8/97* (2013.01); *A61K 8/342* (2013.01); *A61K 8/345* (2013.01); *A61K 8/362* (2013.01); *A61K 8/37* (2013.01); *A61K 8/498* (2013.01); *A61K 8/4973* (2013.01); *A61K 8/602* (2013.01); *A61K 8/891* (2013.01); *A61K 8/922* (2013.01); *A61Q 19/007* (2013.01); *A61Q 19/02* (2013.01); *A61Q 19/08* (2013.01); *A61K 2800/592* (2013.01)

(58) Field of Classification Search
None
See application file for complete search history.

(56) References Cited

U.S. PATENT DOCUMENTS

| | | |
|---|---|---|
| 6,821,524 B2 | 11/2004 | Marini |
| 8,318,678 B2 | 11/2012 | Marini |
| 2007/0196318 A1 | 8/2007 | Marini |
| 2009/0263513 A1 | 10/2009 | Marini |
| 2010/0247693 A1 | 9/2010 | Marini |
| 2013/0189211 A1 | 7/2013 | Marini |
| 2014/0228291 A1 | 8/2014 | Subhash et al. |

FOREIGN PATENT DOCUMENTS

| | | |
|---|---|---|
| EP | 1203579 A1 | 5/2002 |
| EP | 1369107 A1 | 12/2003 |
| EP | 1825845 A1 | 8/2007 |
| WO | 2009/148551 A1 | 12/2009 |

*Primary Examiner* — Qiuwen Mi
(74) *Attorney, Agent, or Firm* — Pamela J. Sherwood; Bozicevic, Field & Francis LLP

(57) ABSTRACT

The present invention features novel cosmetic skin care compositions for improving the appearance of skin.

6 Claims, 1 Drawing Sheet
(1 of 1 Drawing Sheet(s) Filed in Color)

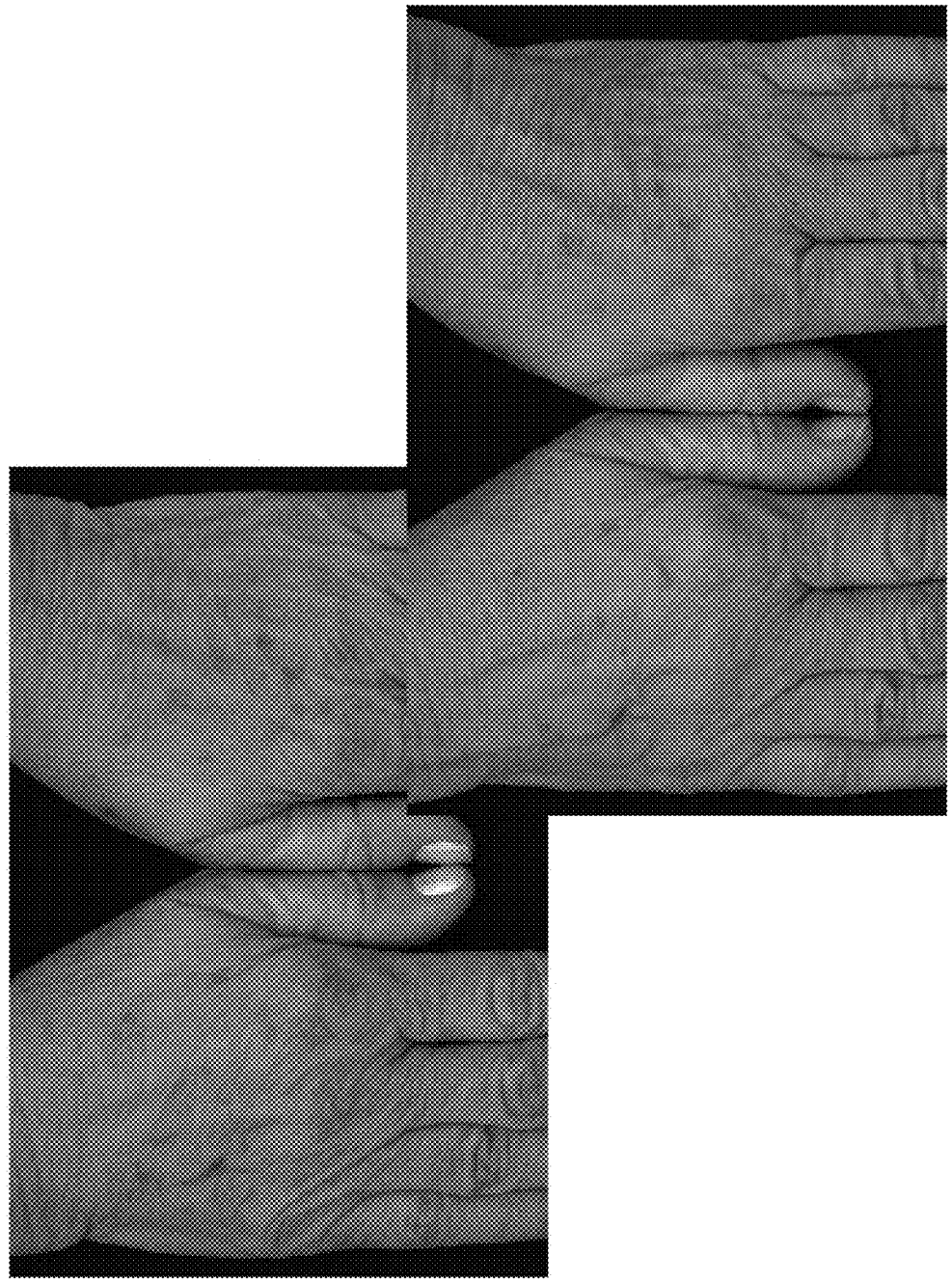

LUMINATE HAND CREAM

BACKGROUND OF THE INVENTION

The skin provides the first barrier to the external environment, and as such it is continually subjected to stresses such as extreme heat or cold, attack by microorganisms, exposure to UV radiation, abrasion, chemical irritants and the like. As a result, the skin can show signs of response to damage over time, for example sunburn, roughening, wrinkling, discoloration, and even malignancies, including basal cell carcinoma, squamous cell carcinoma and melanoma. While these effects are often considered to be normal aging, in fact, they are not normal results of aging but are responses to damage.

A myriad of changes are associated with aging, ranging from hormonal changes to the effects of cumulative sun damage to the continued effects other environmental and social stresses. The signs of progressive aging begin to manifest in the mid 20s, and continue to increase with time. Some of the changes associated with aging included decreased epidermal (top layer of skin) cell turnover; impaired barrier function in the skin leading to moisture loss and risk of irritation; thinning of the dermis; thinning and reduction in elastin fibers (provides skin elasticity); changes and reduction in collagen fibers (structure of the skin); decreased vascular supply to the surface of the skin; cumulative sun damage; significant decline in the skin's immune function inhibiting cellular repair; inflammation and free radical activity causing cellular damage and abnormalities; discoloration, uneven pigment distribution and gradual loss of skin translucency.

In particular, the hands can show the effects of aging, with weathered-appearing hands showing age spots and loss of fat. The cosmetic formulation of the invention address specific needs of aging skin.

SUMMARY OF THE INVENTION

The present invention provides cosmetic formulations for improving the appearance of the skin, including the hands. The cosmetic formulations improve the appearance of signs of aging, including treating wrinkles and aging signs of the hands, as well as reducing undesirable pigmentation such as age spots, etc., associated with aging. The composition is topically administered as a lotion or cream for a period of time sufficient to accomplish the desired effect. In some embodiments the composition is administered once daily, or twice daily, and for at least about one week, at least about two weeks, at least about one month, or longer as desired.

Specifically, the skin care compositions presented herein contain a combination of botanical agents, combined with moisturizing agents, antioxidants and agents for lightening the skin, improving texture and brightening.

The formulation is provided in a cosmetically acceptable vehicle(s), which may further comprise skin soothing/conditioning agents. Accordingly, the combinations of the active ingredients of the invention are formulated as skin care cosmetic compositions that can be applied directly to the skin so as to improve the appearance of skin texture and color. The compositions may additionally provide cosmetic benefit for aging skin, spider veins, and sun damage.

According to the first aspect of the invention, there is provided a cosmetic composition comprising a specific and efficacious blend of moisturizing agents, including the herbal extracts and oils: *Helianthus annuus* (Sunflower) seed oil, *Limnanthes alba* (Meadowfoam) seed oil, *Arnica montana* flower extract, *Cucumis sativus* (cucumber) fruit extract; and retinol, azelaic acid, ascorbyl palmitate and tocopheryl acetate. Hyperpigmentation agents include a blend of botanical extracts *Glycyrrhiza glabra* (licorice) root extract and *Punica granatum* (pomegranate) extract; blended with alpha arbutin, kojic dipalmitate, dipotassium glycyrrhizate, and hexylresorcinol.

In the second aspect of the invention, a method is provided for improving the appearance of the skin, in particular for firming and improving the appearance of the skin of the hands, the method comprising applying topically a cosmetic composition comprising: *Helianthus annuus* (Sunflower) seed oil, *Limnanthes alba* (Meadowfoam) seed oil, *Arnica montana* flower extract, *Cucumis sativus* (cucumber) fruit extract; and retinol, azelaic acid, ascorbyl palmitate and tocopheryl acetate; and *Glycyrrhiza glabra* (licorice) root extract and *Punica granatum* (pomegranate) extract; blended with alpha arbutin, kojic dipalmitate, dipotassium glycyrrhizate, and hexylresorcinol.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a comparison of test subject hands treated with the compositions of the present invention daily for 3 months, showing improved appearance of wrinkles and undesirable pigmentation.

DETAILED DESCRIPTION OF THE EMBODIMENTS

Topical compositions are provided for improving the appearance of the skin, including age-weathered skin of the hands. The cosmetic formulations improve the appearance of signs of aging, including softening the appearance of deep wrinkles and creases; reducing the appearance of fine lines; and improving texture of the skin. The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders. The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

Components of the Cosmetic Compositions

The hand creams of the invention comprise a blend of botanical oils and extracts, formulated with antioxidants and lightening agents. Botanical oils and extracts include *Helianthus annuus* (Sunflower) seed oil, which may be present in the composition at a final concentration of from about 2% to about 10% by weight, usually about 4% to about 6%, and may be present at about 5% by weight. Sunflower oil is known in the art and commercially available, under CAS number 8001-21-6, from various suppliers.

*Limnanthes alba* (Meadowfoam) seed oil may be present in the composition at a concentration of from about 0.5 to about 2% by weight, usually from about 0.75% to about 1.25%, and may be present at a concentration of about 1%. Meadowfoam seed oil is known in the art and commercially available under CAS #153065-40-8 from various suppliers.

*Arnica montana* flower extract may be present in the composition at a concentration of from about 0.02% to about 0.10% by weight, usually about 0.04% to about 0.06%, and may be present at about 0.05% by weight. *Arnica* flower extracts are known in the art, and commercially available under CAS #68990-11-4, for example Active Organics® Actiphyte® Botanical Extracts.

*Cucumis sativus* (cucumber) fruit extract may be present in the composition at a concentration of from about 0.02% to about 0.10% by weight, usually about 0.04% to about 0.06%, and may be present at about 0.05% by weight. Cucumber extracts are known in the art and commercially available, under CAS #89998-01-6, for example Active Organics® Actiphyte® Botanical Extracts.

Retinol, CAS #68-26-8, (2E,4E,6E,8E)-3,7-dimethyl-9-(2,6,6-trimethylcyclohex-1-enyl) nona-2,4,6,8-tetraen-1-ol, may be present at a concentration of from 0.05% to about 0.5%, usually from about 0.1% to about 0.5%, and may be about 0.3% by weight.

Azelaic acid is a saturated dicarboxylic acid, which may be present in the composition at a final concentration of from about 1% to about 10% by weight, usually about 2% to about 5%, and may be present at about 3% by weight. Azelaic acid is known in the art and commercially available, under CAS number 123-99-9, from various suppliers.

Ascorbyl palmitate is a fat-soluble derivative of ascorbic acid (vitamin C), which antioxidant properties. It may be present in the composition at a concentration of from about 0.5 to about 2% by weight, usually from about 0.75% to about 1.25%, and may be present at a concentration of about 1%. Ascorbyl palmitate is known in the art and commercially available under CAS #137-66-6 from various suppliers.

Tocopherol acetate is the ester of acetic acid and tocopherol (vitamin E). Tocopheryl acetate is not oxidized and can penetrate through the skin to the living cells, where about 5% is converted to free tocopherol and provides beneficial antioxidant effects. It may be present in the composition at a concentration of from about 0.05 to about 0.5% by weight, usually from about 0.075% to about 0.125%, and may be present at a concentration of about 0.1%. Tocopheryl acetate is known in the art and commercially available under CAS #7695-91-2 from various suppliers.

Antioxidants and lightening agents in the formulation may include alpha arbutin at a concentration of from about 0.5% to about 5%, usually from about 1% to about 3%, and may be about 2% by weight. Alpha-Arbutin (4-Hydroxyphenyl-α-D-glucopyranoside) is a functional active ingredient for skin lightening, CAS #84380-01-8. Alpha-Arbutin blocks epidermal melanin biosynthesis by inhibiting enzymatic oxidation of Tyrosine and Dopa.

*Glycyrrhiza glabra* (licorice) root extract may be present in the composition at a concentration of from about 0.02% to about 0.10% by weight, usually about 0.04% to about 0.06%, and may be present at about 0.05% by weight. Licorice root extracts are known in the art and commercially available under CAS #84775-66-6, for example Active Organics® Actiphyte® Botanical Extracts.

*Punica granatum* extract (pomegranate) may be present in the composition at a concentration of from about 0.05% to about 0.5%, usually from about 0.1% to about 0.5%, and may be about 0.2% by weight. Pomegranate extract is known in the art, and commercially available under CAS #84961057-9, e.g. formulated with glycerin by Centerchem.

Kojic dipalmitate is an ester of kojic acid and palmitate. Kojic dipalmitate is a fat soluble form, and inhibits the activity of tyrosinase present in human skin so as to inhibit the melanin formation. Kojic dipalmitate which may be present in the composition at a final concentration of from about 2% to about 10% by weight, usually about 4% to about 6%, and may be present at about 5% by weight. Kojic dipalmitate is known in the art and commercially available, under CAS number 79725-98-7, from various suppliers.

Dipotassium glycyrrhizate is a licorice root extract with skin lightening properties. Dipotassium glycyrrhizate may be present in the composition at a concentration of from about 0.5 to about 2% by weight, usually from about 0.75% to about 1.25%, and may be present at a concentration of about 1%. Dipotassium glycyrrhizate is known in the art and commercially available under CAS #68797-35-3 from various suppliers.

Hexylresorcinol is a substituted phenol with skin lightening properties. It may be present in the composition at a concentration of from about 0.5 to about 2% by weight, usually from about 0.75% to about 1.25%, and may be present at a concentration of about 1%. Hexylresorcinol is known in the art and commercially available under CAS #136-77-6 from various suppliers.

The compositions of the invention may further comprise cosmetically useful agents and excipients, e.g. glyceryl stearate, dimethicone, butylene glycol, glycerin, gransil EP-9, plurol diisosteraque, etc. each at a concentration of from about 0.5% to about 10% by weight, usually from about 0.5% to about 5%, and may be present at a concentration of from about 0.5%, 1%, 2%, 3%, 4%, 5%, etc.

The compositions of the invention may optionally comprise other skin benefit materials. These include estradiol; progesterone; pregnanalone; coenzyme Q10; methylsolanomethane (MSM); copper peptide (copper extract); plankton extract (phytosome); kojic acid; broparoestrol; estrone; adrostenedione; androstanediols; hydroquinone; isoflavones; etc. The steroids will generally be present at a concentration of less than about 5% or about 10% of the total by weight of the composition, while the other skin benefit materials may be present at higher levels, for example as much as about 10 to about 15%.

The compositions may further comprise sunscreens to lower skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen, titanium dioxide or zinc oxide may also be used. The exact amount of sunscreen employed in the compositions can vary depending upon the degree of protection desired from the sun's UV radiation.

The amounts of cosmetic or dermatological auxiliaries and additives and perfume to be used in each case can easily be determined by simple exploratory experiments by the person skilled in the art, depending on the nature of the product in question.

Cosmetically Acceptable Vehicle

The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders.

The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc.

Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Accordingly, a composition of the invention comprises a retinoid, a stable kojic acid derivative, and a resorcinol derivative, which may be a synergistic combination, and optionally in combination with one or more of a permeation enhancer, an azelaic acid or a derivative thereof, salicylic acid or a derivative thereof, glycolic acid or a derivative thereof, licorice extract, and green tea extract, and/or a cosmetically acceptable vehicle. Furthermore, a composition of the invention may include additional agents or additives that are not in themselves active agents but play a role in promoting the usefulness or effectiveness of an active agent.

Compositions of the invention may be applied to any subject and used to treat a variety of conditions, for example aged or sun-damaged skin of the hands, for which the compositions may provide firming, and softening of the appearance of wrinkles. A typical composition of the invention is formulated as a solution, lotion, cream, gel, ointment, liniment, solvent, emulsion, dispersion, hydrodispersion, etc., which may be applied topically to the skin so as to treat, prevent, wash, condition or otherwise effect a condition of the skin.

Product Use, Form, and Packaging

In use, a quantity of the composition, for example from 1 to 100 ml, is applied to a site of interest from a suitable container or applicator and, if necessary, it is then spread over and/or rubbed into the site using the hand or fingers or a suitable device. The product may be specifically formulated for use as a treatment for a specific area, e.g. the neck, the hands, the face, the arms, etc.

The cosmetic composition of the invention can be formulated in any form suitable for application to the site of interest, including a lotion, cream, gel, or the like. The composition can be packaged in any suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

Example 1

Example 1 illustrates a topical composition according to the present invention. The composition can be processed in conventional manner and is suitable for cosmetic use. In particular the compositions are suitable for application to a site of interest for the treatment of a variety of skin conditions.

Marini Luminate Hand Cream Cream

| Active ingredients | concentration by weight |
|---|---|
| *Helianthus annuus* (Sunflower) seed oil | 2% to 10% |
| *Limnanthes alba* (Meadowfoam) seed oil | 0.5 to 2% |
| *Arnica montana* flower extract | 0.02% to 0.10% |
| *Cucumis sativus* (cucumber) fruit extract | 0.02% to 0.10% |
| Retinol | 0.05% to 0.5% |
| Azelaic acid | 1% to 10% |
| Ascorbyl palmitate | 0.5% to 2% |
| Tocopherol acetate | 0.05% to 0.5% |
| Alpha arbutin | 0.5% to about 5% |
| *Glycyrrhiza glabra* (licorice) root extract | 0.02% to 0.10% |
| *Punica granatum* extract (pomegranate) | 0.05% to 0.5% |
| Kojic dipalmitate | 2% to 10% |
| Dipotassium glycyrrhizate | 0.5 to 2% |
| Hexylresorcinol | 0.5 to 2% |

Additional ingredients can be included to provide a cosmetically acceptable vehicle, and may comprise water, glycerin, caprylic/capric triglyceride, glyceryl stearate, *Butyrospermum parkii* (shea) butter, cetyl alcohol, dimethicone, cyclopentasiloxane, citric acid, *Prunus amygdalus dulcis* (sweet almond) oil, cyclohexasiloxane, *Glycine soja* (soybean) oil, sodium stearoyl glutamate, squalane, aluminum starch octenylsuccinate, pentylene glycol, sodium oleate, hydrogenated lecithin, ethyl alcohol, coco-glucoside, capryl glycol, sodium citrate, ethylhexylglycerin, hexylene glycol, acrylates/c10-30 alkyl acrylate crosspolymer, xanthan gum, triethanolamine, disodium edta, phenoxyethanol.

In a clinical study report, subjects tested the Luminate hand cream, applied to the hands twice daily for a period of three months. A sample photograph showing improved appearance is provided in FIG. 1.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical application comprising:
from 2-10% *Helianthus annuus* seed oil; from 0.5% to 2% *Limnanthes alba* seed oil; from 0.02-0.1% *Arnica montana* flower extract; from 0.02% to 0.1% *Cucumis sativus* fruit extract; from 0.05% to 0.5% retinol; from 1% to 10% azelaic acid; from 0.5% to 2% ascorbyl palmitate; from 0.05% to 0.5% tocopherol acetate; from 0.5% to 5% alpha arbutin, from 0.02% to 0.1% *Glycyrrhiza glabra* root extract; from 0.05% to 0.5% *Punica granatum* extract; from 2% to 10% kojic dipalmitate; from 0.5% to 2% dipotassium glycyrrhizate; and from 0.5% to 2% hexylresorcinol; and
a cosmetically acceptable vehicle wherein the cosmetically acceptable vehicle is a cream.

2. The composition of claim 1, further comprising from 0.5 to 5% by weight glyceryl stearate.

3. The composition of claim 1, further comprising from 0.5 to 5% by weight dimethicone.

4. The composition of claim 1, further comprising from 0.05 to 0.5% by weight gransil EP-9.

5. The composition of claim 1, further comprising from 0.05% to 0.5% by weight polyglyceryl-3 diisostearate.

6. The composition of claim 1, comprising by weight:
from 4-6% *Helianthus annuus* seed oil; from 0.75% to 1.25% *Limnanthes alba* seed oil; from 0.04% to 0.06% *Arnica montana* flower extract; from 0.04% to 0.06% *Cucumis sativus* fruit extract; from 0.1% to 0.5% retinol; from 2% to 5% azelaic acid; from 0.75% to 1.25% ascorbyl palmitate; from 0.075% to 0.125% tocopherol acetate; from 1% to 2% alpha arbutin; from 0.04% to 0.06% *Glycyrrhiza glabra* root extract; from 0.1% to 0.5% *Punica granatum* extract; from 4% to 6% kojic dipalmitate; from 0.75% to 1.25% dipotassium glycyrrhizate; and from 0.75% to 1.25% hexylresorcinol; and
a cosmetically acceptable vehicle wherein the cosmetically acceptable vehicle is a cream.

* * * * *